United States Patent [19]

McLaurin et al.

[11] Patent Number: 4,812,293

[45] Date of Patent: Mar. 14, 1989

[54] VACUUM ACTUATED ASSAY DEVICE AND METHOD OF USING SAME

[75] Inventors: Daniel A. McLaurin, Cary; Beverly M. Fleming, Raleigh; James P. O'Connell, Chapel Hill, all of N.C.

[73] Assignee: Becton, Dickinson and Company, Franklin Lakes, N.J.

[21] Appl. No.: 159,485

[22] Filed: Feb. 22, 1988

Related U.S. Application Data

[63] Continuation of Ser. No. 880,454, Jun. 30, 1986, abandoned.

[51] Int. Cl.⁴ .............................. G01N 1/18; B01L 3/00
[52] U.S. Cl. ........................................ 422/69; 422/58; 422/61; 422/101; 422/102; 436/56; 436/178; 73/863.23; 73/864.02; 73/864.52; 210/406; 210/321.75
[58] Field of Search ............... 422/56, 58, 61, 68, 422/101, 102; 436/56, 177, 178; 210/321.1, 406, 433.2; 73/61.1 R, 863.23, 864.01, 864.02, 864.52

[56] References Cited

U.S. PATENT DOCUMENTS

| | | | |
|---|---|---|---|
| 3,850,174 | 11/1974 | Ayres | 422/103 X |
| 4,066,512 | 1/1978 | Lai et al. | 435/4 X |
| 4,116,066 | 9/1978 | Mehl et al. | 73/864.52 |
| 4,192,919 | 3/1980 | Raghavachari | 422/101 X |
| 4,200,690 | 4/1980 | Root et al. | 435/7 |
| 4,277,560 | 7/1981 | Gray et al. | 436/807 X |
| 4,300,404 | 11/1981 | Mehl et al. | 73/864.52 X |
| 4,577,514 | 3/1986 | Bradley et al. | 436/177 X |

FOREIGN PATENT DOCUMENTS 0141547 5/1985 European Pat. Off.

OTHER PUBLICATIONS

Millipore catalogue, pgs. 24,26,28,36-37.

Primary Examiner—Michael S. Marcus
Assistant Examiner—Kummert, Lynn M.
Attorney, Agent, or Firm—Richard E. Brown

[57] ABSTRACT

A method for assay of an analyte and assay device therefor. The assay device includes an assay component affixed to a permeable membrane. The membrane preferably rests on a permeable membrane support and covers an opening through a receptacle for holding a liquid. The support is adjacent the open upper end of a double ended needle, the lower end of which is adapted to puncture a plug inserted in an open end of a preevacuated container. Puncturing of the plug establishes fluid communication between the prevacuated interior of the container and the opening in the receptacle whereby liquid in the receptacle is passed through the membrane. The membrane has a bubble point sufficient to prevent passage of air through the membrane after all of the liquid has been pulled through as long as the membrane remains wet so that vacuum in the tube is not lost. The device may be part of an assay workstation which comprises a canister and various utensils useful in performing the assay.

27 Claims, 10 Drawing Sheets

VACUUM ACTUATED ASSAY DEVICE AND METHOD OF USING SAME

This application is a continuation of application Ser. No. 880,454, filed June 30, 1986, now abandoned.

FIELD OF THE INVENTION

This application relates to assay for an analyte. More particularly, it relates to a device for carrying out an assay and to a method for solid phase immunoassay of an analyte.

BACKGROUND OF THE INVENTION

In recent years, many procedures and devices have been disclosed for assay of a substance in a fluid. In particular, assay of biological fluids for substances therein has been the subject of much attention. Among the classes of substances for which assays have been disclosed are endogenous substances such as hormones and antibodies, and exogenous substances such as antigens or drugs. Such substances to be assayed are frequently present in the biological fluid at very low levels, often in the range of $10^{-10}$ molar or lower.

A particularly useful approach to assay for substances present in such low concentrations is immunoassay. In an immunoassay, advantage is taken of the specific reaction of an antigen for an antibody. Two types of immunoassay are in general use. In the first type of assay, commonly referred to as a homogeneous assay, all assay reagents are eventually combined with no separation steps necessary during the procedure. In the second type of assay, commonly referred to as a heterogeneous assay, one or more separation steps are required.

Heterogeneous assays are often performed by fixing or immobilizing one of the assay reagents to an appropriate insoluble solid support. Particularly useful solid supports are microporous membranes as described in U.S. Pat. No. 4,066,512. Such membranes may be subjected to any number of sequentially performed assay steps involving separation and washing of assay components. U.S. Pat. No. 4,200,690 to Root et al. describes assay for an antigen using an antibody immobilized on such a membrane. Assays performed in this fashion are generally referred to as flow-through assays. Separations in such assays conventionally have been performed by allowing a fluid phase to filter through the membrane by gravity. However, since such assays frequently require repeated washing between steps, an excessively long assay time may be required. Exemplary of an assay using gravity flow of liquid is U.S. Pat. No. 4,111,754 to Park.

Various methods have been developed to induce more rapid filtration. U.S. Pat. No. 4,277,560 to Gray et al. discloses a method and apparatus for performing flow-through assay by application of pressure. Chen et al., in U.S. Pat. No. 4,090,850 teaches an apparatus for radioimmunoassay in which antibody coated cellulose discs serve as a solid support in a flow-through assay using multiple wells in a receptacle plate connected to an external vacuum source. Bagshawe, in U.S. Pat. No. 3,888,629, teaches a device in which an assay membrane is in contact with an absorbant material so that filtration of assay fluids into a defined volume is facilitated by capillary action. U.S. Pat. No. 4,246,339 to Cole et al. uses capillary action as a filtration aid in a test device having membranes in multiple assay wells which can be biased into and out of contact with an absorbent material.

European Patent Application No. 0141547 discloses a device in which immunoassay reactions are carried out in a liquid phase above a filter membrane and assay reaction products are filtered using a preevacuated tube as vacuum source.

The use of vacuum to promote flow of an assay fluid through a membrane and to collect the fluid in an absorbent material localized in a defined volume was also known to Applicants at the time of the present invention.

Thus, it is known to use permeable membranes as solid supports in immunoassay procedures and a filters to remove immunoassay reaction products from fluid assay phases. It is further known that a wet filter exhibits properties related to surface tension which are similar to the properties of an array of liquid-filled capillaries and that air will not pass through a wet filter until the pressure on the filter exceeds the capillary attraction of the fluid in the pores of the filter. This pressure is conventionally referred to as the "bubble point," and is defined as the pressure required to blow the first bubble detectable by its rise through a layer of liquid covering the filter. The bubble point, which is easily determined, is a reliable measure of membrane integrity and is generally expressed in $kg/cm^2$, $lbs/in^2$ or bars, wherein one bar equals 14.5 $lbs/in^2$. A general discussion of the bubble point, determination thereof and values for representative filter membranes are given in Millipore Laboratory Products Catalogue, Millipore Corporation, Bedford, Mass., 1982, pages 28 and 36–37.

SUMMARY OF THE INVENTION

A device for assay of an analyte comprises a reacting unit, a collecting unit and a vacuum actuating unit. The reacting unit includes a permeable membrane having an assay component affixed thereto, a membrane support and liquid holding means adjacent the membrane. The membrane rests on the support, which has fluid communication means therethrough. Included in the collecting unit is preevacuated liquid collecting means. The vacuum actuating unit includes means for establishing fluid communication between the collecting means and the membrane support. When fluid communication is established, liquid in the holding means is directed through the membrane and support and into the collecting means, but air, when all of the liquid has passed through, is inhibited from passing through the wet membrane as long as the bubble point has not been exceeded.

In a preferred embodiment of the invention, the holding means is a cylinder having a substantially conical cavity; the collecting means is a preevacuated container or tube having a closed end and an open end with a puncturable plug therein, and the actuating means is a hollow double ended needle affixed to a needle housing adjacent the lower edge of the support. The interior of the needle housing is slidably mounted over the tube so that downward pressure on the reacting unit causes the lower end of the needle to puncture the plug and establish fluid communication with the support.

In another embodiment of the invention, the needle, after puncturing the stopper, may be locked, as for example by a lip and flange, so that vacuum is continuously maintained. Additional structure, as for example a spring, may be provided to retract the needle so that the vacuum may be alternately applied to and released from the membrane.

The device may be part of an assay work station which includes other components useful in performing an assay, such as tubes, droppers vials and the like. These components may include assay reagents, such as, for instance, labeled antibodies and chromogens.

The assay device of the invention overcomes significant disadvantages associated with prior art devices. Thus, the rate at which a liquid can be drawn through a membrane by capillary action is slow and fixed. Enhancement of flow rate by application of pressure or vacuum provided by an external source requires expensive and cumbersome equipment. In contrast, an assay performed with the preevacuated tube of the invention is quick, efficient, clean and, because all waste liquid is collected in a confined space, is sanitary and clean. Further, the combination of a preevacuated tube of defined vacuum and size with a membrane of carefully defined bubble point provides the device of the invention with flexibility unattainable with prior art devices. Thus, flow rates may be controlled in assays using a contained vacuum source without disconnecting the vacuum at any time. By proper selection of membrane and tube, incubation periods can also be varied without disconnecting for prolonged incubations and reapplied at a later time.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

Figure 1:
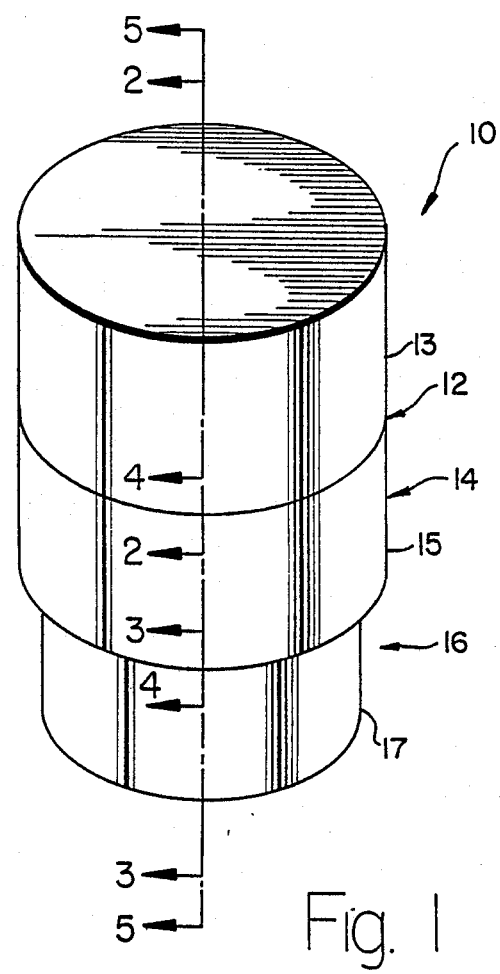
FIG. 1 is a perspective view of the preferred embodiment of the assay device of the invention.

A preferred embodiment of the assay device of the invention will now be described in detail with the aid of the Figures. FIG. 1 illustrates an assay device 10 having a reacting unit 12, covered by a cover 13, a vacuum actuating unit 14 with an enclosure 15 and a collecting unit 16 mounted in a base 17. Base 17 is dimensioned to fit slidably into enclosure 15.

Figure 2:
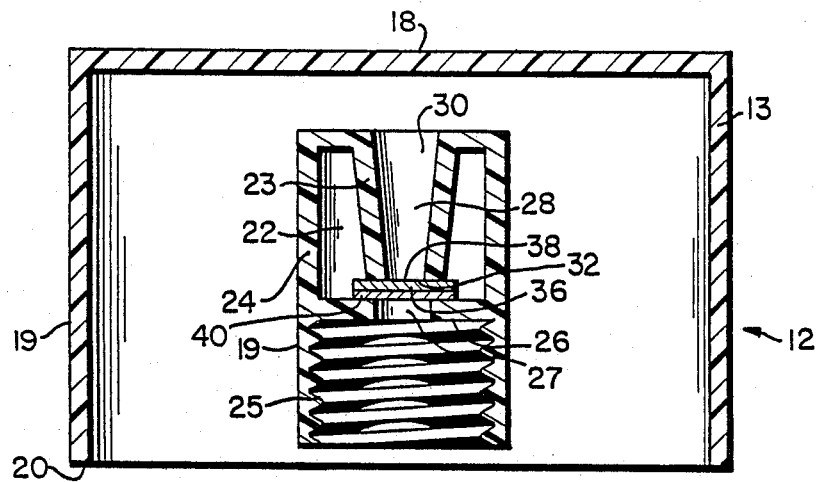
FIG. 2 is a vertical sectional view of the reacting unit of the device of FIG. 1 taken along the line 2—2 thereof.

As seen in FIG. 2, cover 13 has a top portion 18 and a sidewall portion 19 having a flat bottom edge 20. A cylinder 22 has an inwardly tapering wall portion 23, a vertical outside wall portion 24 having a thread 25 on the lower portion thereof and a flat bottom portion 26 having an aperture 27 therethrough. Wall portion 23 defines a cone 28, which has an open upper end 30 and an open lower end 32 of smaller diameter than upper end 30. Tapered wall portion 23 of cone 28 ends at open lower end 32 so that end 32 is adjacent and in fluid contact with a membrane 36 having affixed thereto an assay reagent 38. Membrane 36 rests on a membrane support 40.

Membrane support 40 may be of any material of sufficient rigidity to support membrane 36 while at the same time providing permeability so that fluid communication is established between membrane 36 and collecting unit 16. A preferred form for support 40 is a permeable disc or a solid disc having a hole therethrough for fluid communication, or most preferably support 40 may be integrally formed with cylinder 22.

Figure 3:
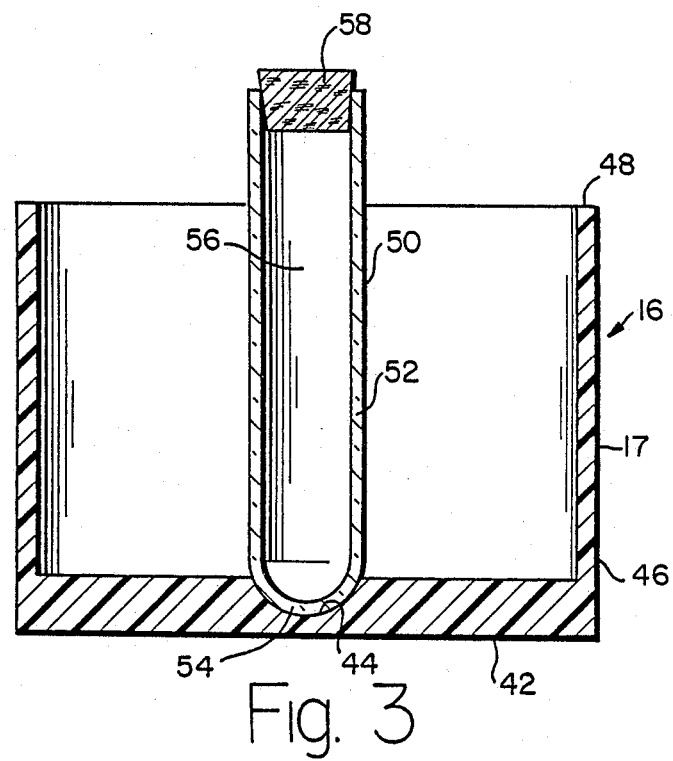
FIG. 3 is a vertical sectional view of the collecting unit of the device of FIG. 1 taken along the line 3—3 thereof.

Details of collecting unit 16 are depicted in FIG. 3. Collecting unit 16 includes base 17 having a bottom portion 42 with a depression 44 and a sidewall portion 46 having a flat top surface 48. Unit 16 preferably has a preevacuated tube 50 defined by a wall portion 52, a closed bottom end 54 and an open upper end 56 having a puncturable, preferably self-sealing, stopper 58 therein. Depression 44 is dimensioned to receive bottom end 54 of tube 50. Preevacuated collecting tubes with puncturable stoppers are well-known in the art and are commercially available. They are manufactured and sold by Becton, Dickinson and Company under the trade name Vacutainer ® evacuated tubes. The tube of the present invention may be any volume sufficient to hold all of the fluid contemplated to be used in the assay and may be of any pressure such that the effective bubble point of the membrane, as defined later, is sufficient to prevent any substantial passage of air through the membrane when wet. The preferred tube has a volume of from 3 to 15 ml and preevacuated pressure of from 0.1 to 0.9 $kg/cm^2$, most preferably from 0.279 to 0.785 $kg/cm^2$.

Figure 4:
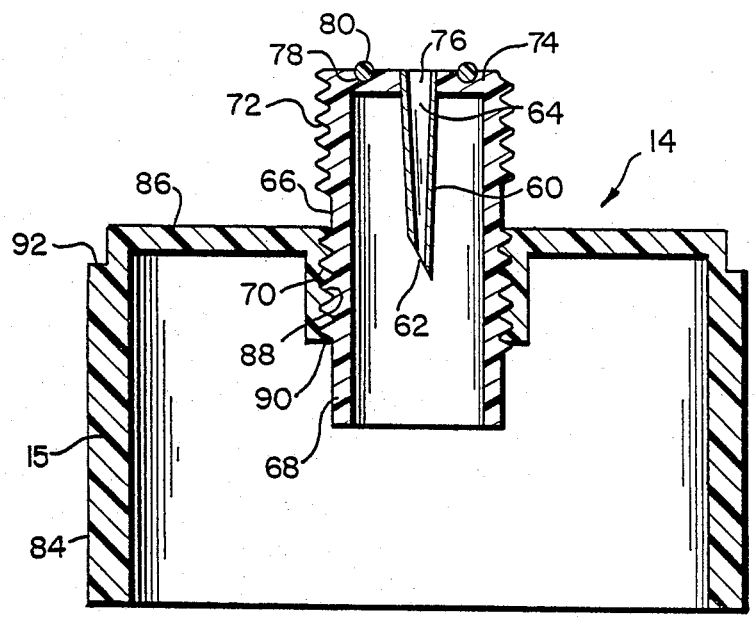
FIG. 4 is a vertical sectional view of the vacuum actuating unit of the device of FIG. 1 taken along the line 4—4 thereof.

FIG. 4 illustrates the details of vacuum actuating unit 14. A needle 60 has an open lower end 62 and an open upper end 64 and is mounted in a needle housing 66. Housing 66 has a wall portion 68 with a first external thread 70, a second external thread 72 and a top portion 74. Top portion 74 is preferably in the form of a disc having a hole 76 into which needle upper end 64 is inserted. Disc 74 has a groove 78 recessed therein. An O-ring 80 is snugly positioned in groove 78.

Enclosure 15 has a vertical wall portion 84 and a flange 86. An internal thread 88 on an inside wall portion 90 of flange 86 is mated with external thread 70 of needle housing wall portion 68. Flange 86 has a notch 92 in wall portion 84.

Figure 5:
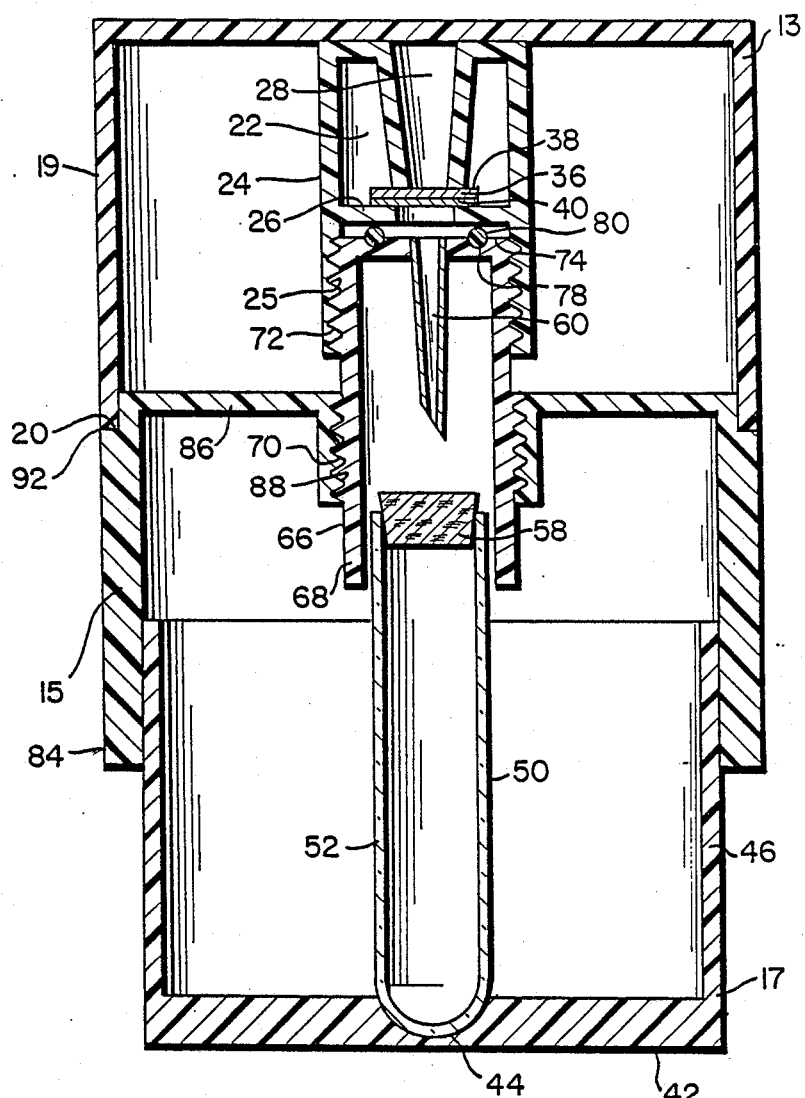
FIG. 5 is a vertical sectional view showing the relationship of the reacting, collecting and vacuum actuating units of FIGS. 2, 3 and 4 respectively taken along the line 5—5 of FIG. 1.

FIG. 5 shows the assembly of the three assay units described above. Preevacuated collection tube 50 is positioned in depression 44 of bottom portion 42 of base 17. Wall portion 68 of housing 66 preferably forms a snug slidable compression fit over wall portion 52 of collection tube 50. Enclosure 15 is secured to housing 66 with mating threads 88 and 70 on flange 86 and housing wall portion 68 respectively. It is seen that vertical wall portion 84 of enclosure 15 fits over sidewall portion 46 of base 17.

Top portion 74 of housing 66 is adjacent flat bottom portion 26 of cylinder 22 and sealably connected thereto by O-ring 80 in groove 78. Membrane 36, having assay component 38 affixed thereto, is placed on support 40. Cylinder 22 is secured to housing 66 with mating threads 25 and 72 of cylinder wall portion 24 and housing wall portion 68 respectively. Cover 13 is positioned over cylinder 22 so that flat bottom edge 20 of sidewall portion 19 fits into notch 92 of flange wall portion 84. It is seen that, when assembled as described above, needle 60 remains above stopper 58 when housing wall portion 68 and tube wall portion 52 are compression-fit together.

Figure 6:
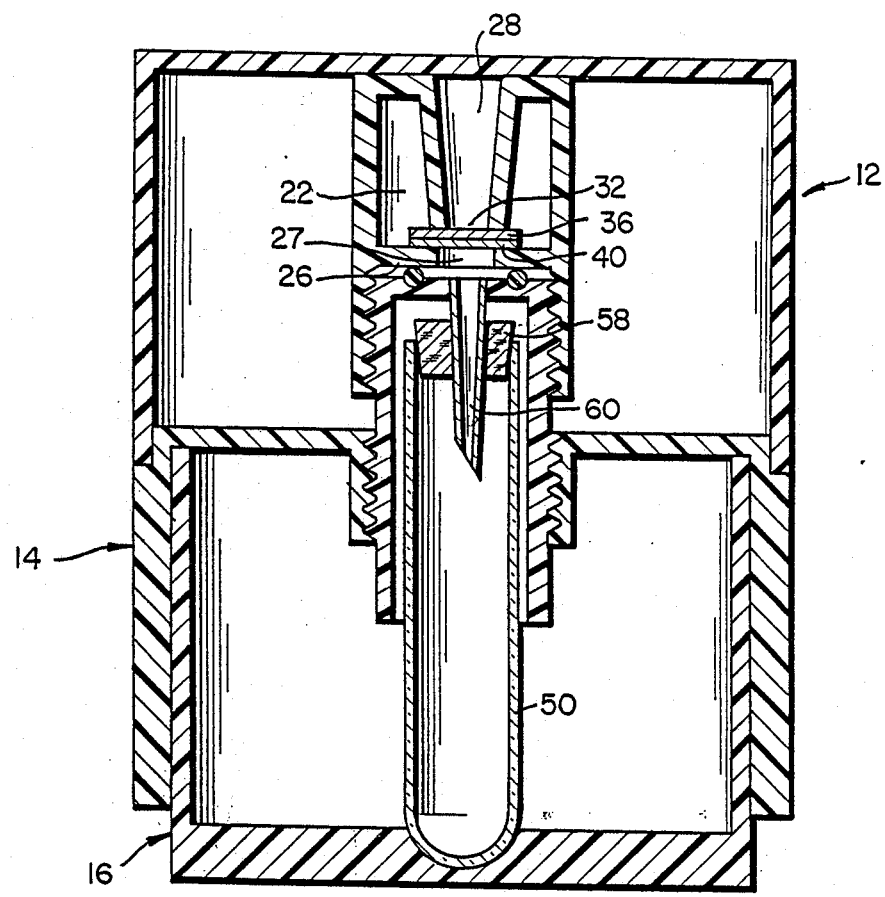
FIG. 6 is a vertical sectional view taken along line 5—5 of FIG. 1 showing the relationship of the reacting, collecting and vacuum actuating units of FIGS. 2, 3 and 4 respectively after actuation of the vacuum.

For use of the device in an asasy, cover 13 is removed and assay reagents are added to cone 28 and a suitable time allowed for any desired reaction to take place. In order to remove liquid from cone 28, slight downward hand pressure on cylinder 22 causes housing wall portion 68 to slide downward in contact with tube wall portion 52 so that needle 60 punctures stopper 58 thereby establishing fluid communication between vacuum in tube 50 and liquid in cone 28. FIG. 6 depicts the device after needle 60 punctures stopper 58. The liquid passes through membrane 36, support 40 and needle 60 into tube 50. When all of the liquid has passed into tube 50, air is inhibited from passing through the wet membrane by the membrane bubble point. Subsequent assay steps, such as washings or addition of color forming reagent solutions, may thus be carried out without loss of the vacuum. If desired, needle 60 may be removed from tube 50 merely by applying upward hand pressure to the combined reacting unit 12 and actuating unit 14 and reinserted at a later time. This feature allows significant flexibility in assay design wherein any step requiring a long time to perform can be done with the vacuum disengaged.

Figure 7:
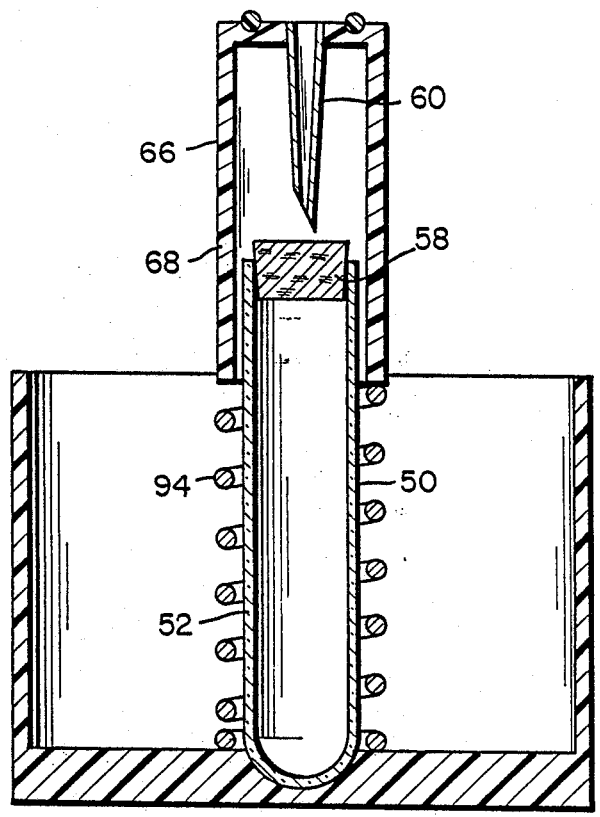
FIG. 7 is a vertical sectional view similar to FIG. 3 illustrating an embodiment thereof having structure for alternate insertion and retraction of the needle through the plug.

The invention contemplates a variety of other designs for the assay device. For example, the units of the device can be attached by screw fits, snap fits and the like instead of the threaded fits described in detail above. The slidable compression fit between wall portions 68 and 52 may be replaced by a spring surrounding the tube as shown in FIG. 7. In this embodiment of the device, downward pressure on cylinder 22 causes wall portion 68 of housing 66 to engage and compress a spring 94 whereby needle 60 punctures plug 58. The downard pressure may be maintained until all fluid is removed from the cone, whereupon, on release of the pressure, spring 94 releases causing needle 60 to exit from plug 58. Alternatively, a locking mechanism may be present (although not shown in the drawings) so that, when spring 94 is compressed, needle 60 is held in plug 58 and vacuum to the cone is maintained until the locking mechanism is released.

In still another embodiment of the device, base 17 may be eliminated and needle puncture effected by upward pressure on tube 50. This design is particularly useful when only a single needle puncture is contemplated, and advantageously includes a modified tube having a flat bottom portion.

In other embodiments of the device various parts may be integral. For example, in a particularly preferred embodiment of the dvice, it is contemplated that cylinder 22 and membrane support 40 may be integrally connected or molded as a single piece. In a related embodiment of the invention, support 40 may be eliminated altogether by using a modified membrane which is self-supporting and which conveniently may rest on flat bottom portion 26 of cylinder 22.

Assay device 10 may be part of an assay workstation. In the following discussion of the workstation, elements of the device which correspond to elements previously described in respect to assay device 10 are given the same base number followed by a lower case letter.

Figure 8:
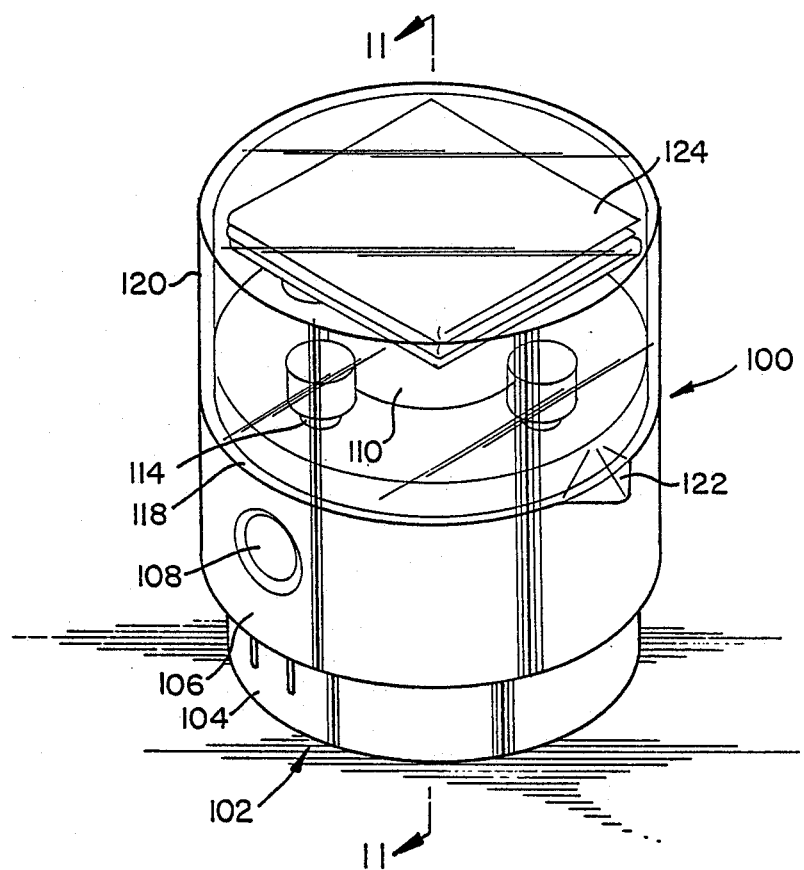
FIG. 8 is a perspective view of one embodiment of a workstation of the invention.
Figure 9:
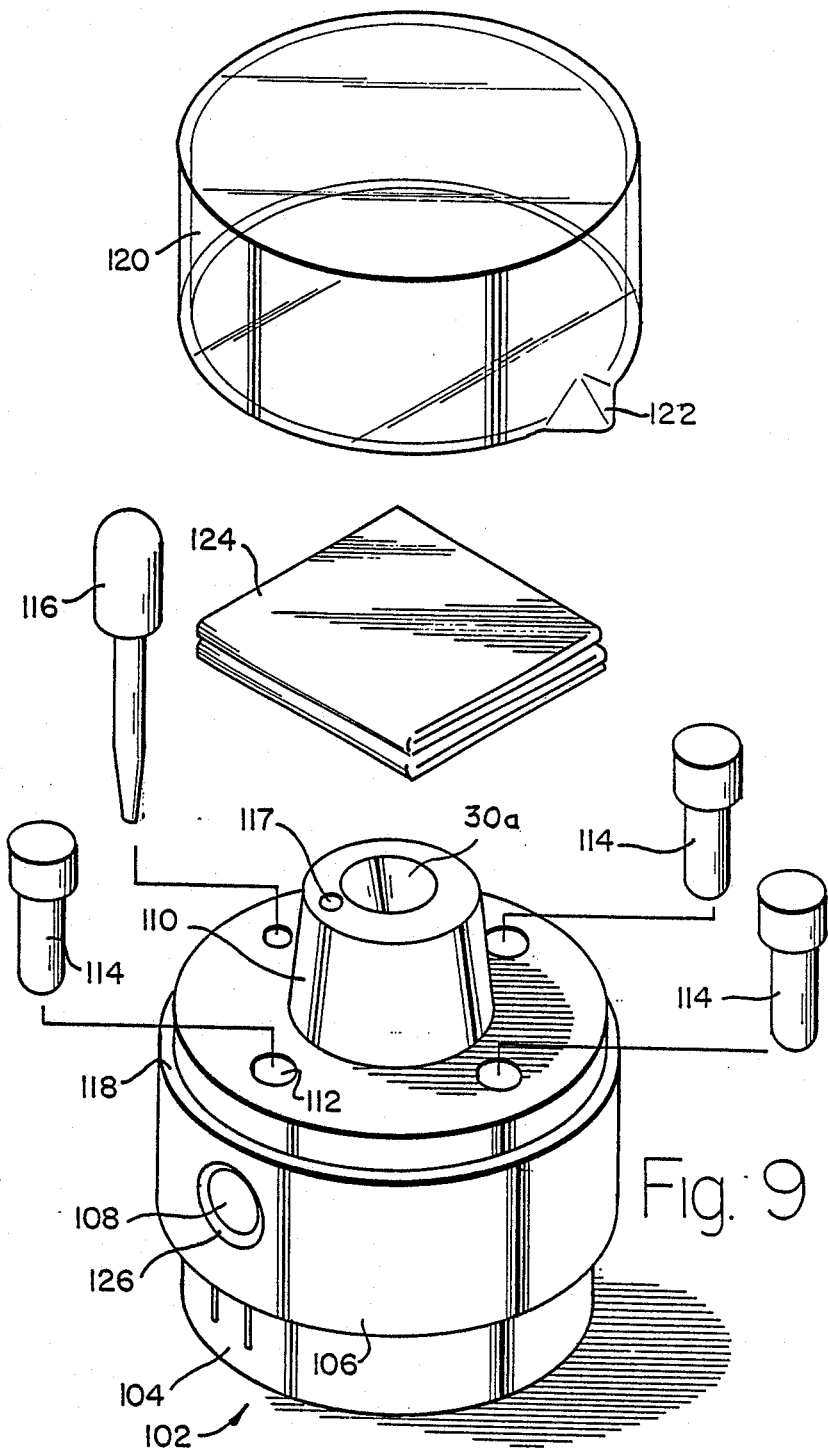
FIG. 9 is an exploded perspective view of the workstation of FIG. 8 showing the parts disassembled.
Figure 10:
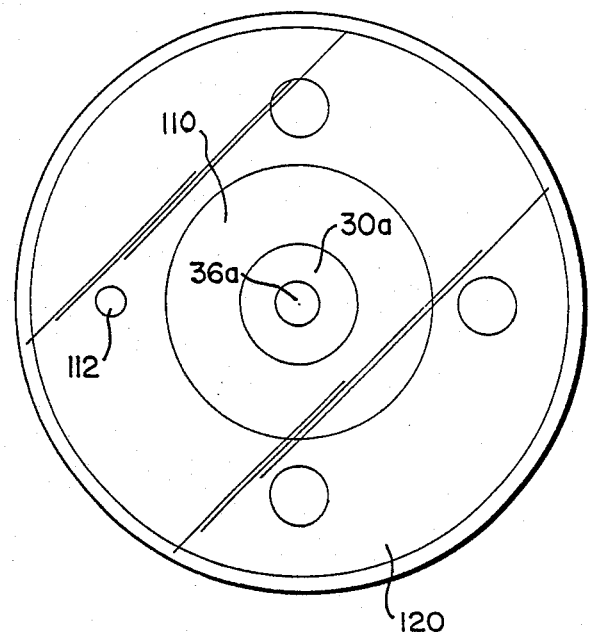
FIG. 10 is a top plan view of the workstation of FIG. 9.

FIG. 8 illustrates the preferred workstation 100 in the assembled and FIG. 9 shows representative components of the workstation in a dissembled condition. A canister 102 has a base 104 and a body portion 106 dimensioned to fit over base 104 and held in position to prevent premature needle penetration by a locking mechanism actuated by a press button 108 (as described below in detail and illustrated in FIG. 11). Body portion 106 has a hole 126 for press button 108 and a top portion 110 which encases open upper end 30a of cone 28a (see FIG. 2), and includes a plurality of holes or recesses 112 which receive assay utensils, such as a vial 114 and a dropper 116. A color dot 117 serves as a reference for an assay in which a color serves as the endpoint. A lip 118 of body portion 106 receives a cap 120. Cap 120 has a pour spout 122 and serves the dual purpose of cap and sample collector. A folded insert 124 may be included in the workstation and may be, for example, instructions for use. FIG. 10 shows cap 120, top portion 110, holes 112, open upper end 30a of cone 28a and membrane 36a.

Figure 11:
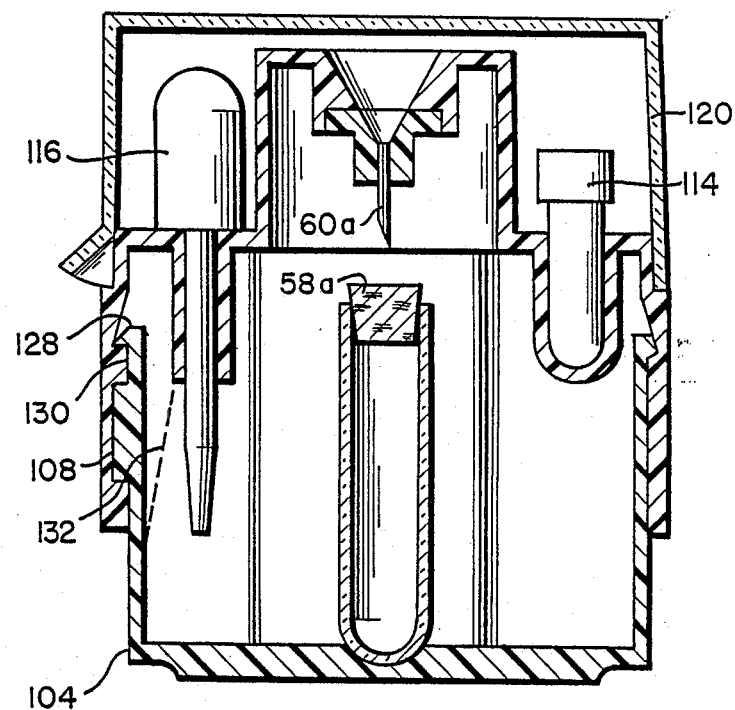
FIG. 11 is a vertical sectional view of the workstation of FIG. 8 taken along the line 10—10 thereof.

FIG. 11 illustrates a locking means to prevent premature specification of the needle into the stopper. Canister base 104 has press button 108 in hole 126 (FIG. 9) of body portion 106 and a catch 128 which engages a flange 130 of body portion 106. To cause penetration of needle 60a into stopper 58a, button 108 is pressed inwardly to occupy a position indicated by a phantom line 132 thereby releasing catch 128 from flange 130. With button 108 in position 132, downward pressure on cap 120 causes needle 60a to puncture stopper 58a.

Permeable membrane 36 has a bubble point sufficiently high to prevent any substantial passage of air therethrough when wet and when used in an assay with preevacuated tube 50 (as described later), and may be of any substance to which an assay component, preferably an immunoassay component, is attachable to give an assay solid phase suitable for flow-through assay. The preferred membrane may have a bubble point of from about 1.5 to 5.0 kg/cm$^2$, most preferably from 2.0 to 3.5 kg/cm$^2$, and has a high surface to volume ratio so that sufficient assay component 38 can be affixed thereto. Preferred membranes are polycarbonate and glass fiber. Particularly preferred membranes are nitrocellulose or nylon.

Reagent 38 may be any assay component which can be affixed to membrane 36. In general, reagent 38 may be an antianalyte specific to an analyte to be assayed. In the preferred immunoassay of the invention, reagent 38 may be an antigen, or preferably an antibody specific to an antigen analyte. If, on the other hand, the analyte is an antibody, reagent 38 may be a specific antigen thereto. The choice of reagent 38 thus depends on the nature of the analyte. Any conventional method of affixing reagent 38 to membrane 36, such as covalent coupling or physical absorption may be employed. These methods are well-known in the art and no further details in this regard are needed for a complete understanding of the invention. Further details of the role of reagent 38 in assays performed with the device of the invention are provided later in the description of suitable assay formats and in the Examples.

The bubble point of a membrane is the pressure required to force a gas, such as air, through the membranes when wet. It is evident that the bubble point pressure has two components, the standard one atmosphere to which any membrane is subjected at sea level, and the additional pressure required to overcome the capillary attraction of the fluid in the membrane. If the pressure on the lower surface of the membrane is less than the pressure exerted on the upper surface, the effective bubble point, i.e., the pressure which actually determines whether or not air will pass through the wet membrane will be less than the defined bubble point by this pressure differential across the membrane.

In accordance with the present invention, it has been found that gases, such as air, will not pass through membrane 36 even when vacuum from preevacuated tube 50 is applied as long as the membrane remains wet and the effective bubble point of the membrane is not exceeded. Because of this feature, a number of sequential manipulations may be performed (such as incubation, washing, etc.) on the membrane without loss of vacuum in the tube.

The effective bubble point of the membrane may be calculated by the simple formula BPE=BP−PD wherein BP is the membrane bubble point as defined, BPE is the effective bubble point and PD is the pressure differential across the membrane, i.e., the difference between atmospheric pressure and the tube pressure all in $kg/cm^2$. Thus, it may be determined from the defined bubble point of the membrane and the known tube pressure whether a given combination of tube and membrane are operative in the invention. For example, using a preferred nitrocellulose membrane of the invention having a bubble point of 2.5 bars, or 2.55 $kg/cm^2$ and a preevacuated tube having a pressure of 0.279 $kg/cm^2$, it is readily seen that the pressure differential across the membrane is atmospheric pressure (1.033 $kg/cm^2$) less tube pressure (0.279 $kg/cm^2$) or 0.754 $kg/cm^2$. The effective bubble point of this membrane when wet and subjected to this vacuum is thus 2.55 less 0.754 or 1.796 $kg/cm^2$, well above atmospheric pressure so that air will not pass through the wet membrane and destroy the vacuum in the tube.

It is evident that vacuum in the tube decreases each time fluid passes into the tube. For this reason, at no time during an assay will the effective bubble point be exceeded and vacuum lost, and a complete assay can be carried out without breaking the vacuum provided the tube has a volume sufficient to receive all assay fluid to be pulled through the membrane.

The rate at which a fluid is drawn through the membrane by the vacuum in the tube depends on the bubble point of the membrane and the vacuum in the preevacuated tube. Thus, by proper choice of membrane and vacuum, significant flexibility is conferred on assay design. For example, if the assay reaction is rapid so that only short contact is needed, a membrane of low bubble point (high porosity) may be selected. If the assay requires a significant period of contact between a reagent in the fluid and the assay component affixed to the membrane, a membrane of high bubble point (low porosity) may be used. If exceptionally long contact, such as a long incubation, is required, the needle may be withdrawn from the tube, as described above, and reinserted at a later time.

The assay to be performed using the device or workstation of the invention may be configured in various ways known to the art. For example, in a double antibody sandwich assay, reagent 38 may be a first or trapping antibody physically affixed to the membrane, and the membrane placed on the membrane support. A fluid sample containing the analyte, such as serum, urine or any solution of the analyte is a suitable diluent such as saline or buffer, is added to the cone and passed through the membrane by causing penetration of the needle into the preevacuated tube. The fluid may be passed through the membrane at a defined rate based on the strength of the vacuum and the bubble point of the membrane whereby immunological binding of the analyte to the antibody takes place. Alternatively, the analyte and antibody may be held in contact for any incubation period prior to actuation of the vacuum. Analyte thus bound to the trapping antibody is then contacted by a tracer, generally a second or marking antibody, wherein, again, the period of contact between the bound analyte and the tracer is rendered flexible by the feature of the device which allows control of the magnitude and duration of the applied vacuum. With the tracer now bound to the analyte, an appropriate next step may be passage of a reporting material, such as a chromogenic substrate (if the antibody is marked with an enzyme) through the membrane wherein color formation or disappearance indicates a positive reaction and presence of the analyte. As mentioned earlier, in such a color generating reaction, color dot 117 serves as a reference for comparison with the color generated on the membrane. Other reporting systems, for example radioisotopes, fluorescers or liposomes containing a marker, may also be used.

In an alternative configuration of a double antibody sandwich assay, the analyte and tracer may be added together to the fluid in the cone, and, after an appropriate incubation period, the vacuum is actuated and the bound analyte tracer is pulled through the membrane and thereby bound to the trapping antibody on the membrane.

Assays configured according to conventional competitive techniques may also be carried out with the device of the invention. For example, analyte and tracer (generally labeled analyte) may be simultaneously passed through the membrane and thereby bound to the trapping antibody on the membrane in proportion to their concentrations in the fluid.

Analytes which may be assayed advantageously with the device of the invention may be monoepitopic or polyepitopic. Typical analytes may be haptens, such as digoxin, thyroxin and the like, polypeptides such as insulin, hormones such as human chorionic gonadotropin, luteinizing hormone and the like, bacterial antigens, such as group A Streptococcus, and viral antigens such as respiratory syncytial virus, Epstein Barr virus, Herpes simplex virus and the like.

The following examples are provided to further illustrate use of the device of the invention in immunoassay.

EXAMPLE 1

Three ul of antibody directed against Group A Streptococcus antigen were deposited on the center of a microporous nitrocellulose membrane having a nominal pore size of 0.45 micron (Schleicher and Scheull, Keene NH, Type BA/85). The membrane was air dried, soaked for one hour at room temperature in a 5% aqueous solution of bovine serum albumin (BSA), air dried, and positioned on membrane support 40. Group A Strep antigen was extracted by conventional means from a patient throat swab, and a solution of the antigen in 1M tris buffer was mixed in a glass tube with 100 ul of alkaline phosphate-anti Strep antibody conjugate. The mixture was incubated for three minutes at room temperature, then poured into cone 28. Vacuum was applied to the membrane by downward pressure on cylinder 22 to cause needle 60 to penetrate stopper 58 whereby the enzyme labeled conjugate passed through the membrane. One ml of wash buffer (50 mM tris, 1 mM magnesium chloride, 0.1 mM sodium chloride and 0.1% BSA, pH 9.0) was added to the cone and drawn through the membrane, followed by a solution 200 ul of 0.005 M indoxyl phosphate in wash buffer at pH 10.0. A blue dot formed in the center of the membrane, indicating the presence of Group A Strep antigen in the swab extract.

An immunoreactive membrane prepared and treated as above but not exposed to Group A Strep antigen remained colorless.

EXAMPLE II

In the same way as described in Example I, antibody directed against human chorionic gonadotropin (hCG) antigen and BSA were deposited on a disc of BA/85 membrane, and the membrane was positioned on support 40. Patient urine (400 ul) in a glass tube was mixed with 100 ul of alkaline phosphatase-anti hCG antibody conjugate, and the mixture was incubated for three minutes at room temperature. The incubation mixture was added to cone 28 and pulled through the membrane by depressing cylinder 22 to activate the vacuum. The membrane was washed with buffer and a solution of indoxyl phosphate in buffer was passed through the membrane, as described in Example I. A blue dot formed in the center of the membrane, indicating that hCG was present in the urine sample.

An immunoreactive membrane prepared and treated as above with a urine sample devoid of hCG remained colorless or faintly colored.

EXAMPLE III

The experiment of Example II was repeated on a urine sample suspected of containing hCG except the labeled antibody was goat antimouse colloidal gold conjugate. Using this label, a red dot formed in the center of the membrane indicating that hCG was present in the urine sample.

An immunoreactive membrane prepared and treated as above with a urine sample devoid of hCG remained colorless.

Thus, the invention discloses a device for immunoassay in which the vacuum of a preevacuated tube is balanced against the bubble point of a permeable membrane. In this way, vacuum may be used to facilitate assay filtrations without loss of the vacuum by passage of air through the wet membrane. A plurality of separation steps, such as washings, may thereby be performed rapidly and efficiently. The device may include structure whereby the vacuum may be applied for a time, released for any desired length of time, then reapplied at a later time. Significant advantages, in particular, flexibility to configure assays to include variable incubation and washing schedules, accrue from use of the device.

What is claimed is:

1. An assay device comprising:
   (a) a permeable membrane having attached thereto a component of an assay, said membrane having a bubble point of about 1.5 to 5.0 kg/cm$^2$ which allows passage of liquid therethrough but which precludes passage of gas therethrough when a pressure differential exists across said membrane and said membrane is wet;
   (b) liquid holding means having an open end covered by said membrane;
   (c) pre-evacuated liquid receiving means; and
   (d) actuating means between said membrane and said receiving means and removably affixed to said holding means to establish said pressure differential whereby fluid communication between said receiving means and said membrane is established.

2. An assay comprising:
   (a) a permeable membrane having attached thereto an antianalyte specific to an analyte, said membrane having a bubble point of about 1.5 to 5.0 kg/cm$^2$ which allows passage of liquid therethrough but which precludes passage of air therethrough when a pressure differential exists across said membrane and said membrane is wet;
   (b) a receptacle for holding a liquid, said receptacle being defined by a cylinder having a first open end covered by said membrane and a second open end for receiving liquid;
   (c) a pre-evacuated container having a closed end and an open end, said open end having therein a puncturable plug sealing the open end closed; and
   (d) means for puncturing said plug, said means being removably affixed to said receptacle and situated between said membrane and said container, said plug when punctured providing liquid communication between an interior of said container and said membrane whereby liquid passes from said receptacle through said membrane into the interior of said container.

3. The device of claim 2 wherein said receptacle is cone shaped and said first open end is smaller than said second open end.

4. The device of claim 2 wherein said container has a sufficient volume to hold all of the fluid of an assay.

5. The device of claim 2 wherein the initial pressure in said container is no greater than 0.785 kg/cm$^2$.

6. The device of claim 2 wherein said plug is self-sealing.

7. The device of claim 2 wherein said membrane is fabricated from a material selected from the group of materials consisting of nitrocellulose, nylon, polycarbonate and glass fiber.

8. The device of claim 2 wherein said antianalyte is selected from the group consisting of an antibody, an antigen and a lectin.

9. The device of claim 2 further comprising support means for said membrane having fluid communication therethrough.

10. The device of claim 9 wherein said support means is a flat washer having a passageway therethrough.

11. The device of claim 2 wherein said means for puncturing includes a hollow needle open at both ends slidably mounted in a housing means, said housing means being removably affixed to said receptacle.

12. The device of claim 11 further comprising a spring surrounding said container, said spring being compressible by said housing means.

13. The device of claim 11 further comprising housing means for said needle.

14. The device of claim 13 wherein said means for puncturing is removably connected to said housing means.

15. An assay device comprising:
(a) a pre-evacuated tube having a closed end and an open end, said open end having therein a puncturable plug sealing the open end closed, said tube having been evacuated to a pressure of from about 0.279 to 0.785 kg/cm$^2$;
(b) a needle housing having said tube slidably mounted therein;
(c) a double-ended needle having fluid communication therethrough, said needle being affixed at a first end to said needle housing, whereby a second end of said needle is positioned above said plug;
(d) a membrane support having fluid communication therethrough positioned on said housing and adjacent the first end of said needle;
(e) permeable membrane on said support, said membrane having attached thereto an antianalyte specific to an analyte, said membrane having a bubble point of about 1.5 to 5.0 kg/cm$^2$ when wet which precludes passage of air therethrough when said membrane is placed in fluid communication with an interior of said tube when the second end of said needle punctures said plug;
(f) a cylinder having a flat bottom portion and a tapered inner wall portion which defines a cone-shaped receptacle, said cylinder being removably affixed to said housing, said receptacle having a larger open upper end for receiving liquid for an assay and a smaller open lower end covered by said member; and
(g) sealing means connecting said needle housing and said flat bottom portion of said cylinder.

16. The device of claim 15 wherein said membrane is nylon.

17. The device of claim 15 wherein said membrane is nitrocellulose.

18. The device of claim 15 wherein said membrane support and said cylinder are integrally formed.

19. The device of claim 15 wherein said sealing means is an O-ring in a groove in an upper surface of said needle housing.

20. An assay workstation comprising:
an assay device within a housing means, said device including:
(a) a permeable membrane having attached thereto an antianalyte specific to an analyte, said membrane having a bubble point of about 1.5 to 5.0 kg/cm$^2$ which allows passage of liquid therethrough but which precludes passage of air therethrough when a pressure differential exists across said membrane and said membrane is wet;
(b) a receptacle for holding a liquid, said receptacle being defined by a cylinder having a first open end covered by said membrane and a second open end for receiving liquid;
(c) a pre-evacuated container having a closed end and an open end, said open end having therein a puncturable plug sealing the open end closed; and
(d) means for puncturing said plug, said means being removably affixed to said receptacle and situated between said membrane and said container, said plug when punctured providing liquid communication between an interior of said container and said membrane whereby liquid passes from said receptacle through said membrane and into the interior of said container, said housing means having a recess for receiving a utensil useful in performing an assay.

21. The workstation of claim 20 wherein said utensil is a tube.

22. The workstation of claim 20 wherein said utensil is a dropper.

23. The workstation of claim 20 wherein said utensil is a vial.

24. The workstation of claim 20 further comprising an assay reagent in said utensil.

25. The workstation of claim 20 wherein said housing means comprises a cannister having a base and a body portion.

26. The workstation of claim 25 further comprising means for preventing premature puncture of said plug.

27. The workstation of claim 26 wherein said means for preventing premature puncture comprises a catch on said base engaged with a flange on said body portion, said flange being actuated by a press button on said base to disengage from said catch.

* * * * *